United States Patent [19]

Hsu et al.

[11] Patent Number: 5,095,754
[45] Date of Patent: Mar. 17, 1992

[54] APPARATUS AND METHOD FOR DETECTION OF ICING ONSET AND ICE THICKNESS

[75] Inventors: David K. Hsu; Frank J. Margetan; Samuel J. Wormley, all of Ames, Iowa; Jeffrey A. Simpson, 5255 Rockwell Dr., N.E., Cedar Rapids, Iowa 52402

[73] Assignees: Jeffrey A. Simpson, Hiawatha; Theodore A. Johnson, Cedar Rapids, both of Iowa

[21] Appl. No.: 681,740

[22] Filed: Apr. 8, 1991

Related U.S. Application Data

[63] Continuation of Ser. No. 378,851, Jul. 12, 1989, abandoned.

[51] Int. Cl.$^5$ ............................................. G01N 9/24
[52] U.S. Cl. ..................................... 73/602; 340/962
[58] Field of Search ............... 73/602, 597, 632, 644, 73/590, 24.01, 599, 620, 627; 340/962

[56] References Cited

U.S. PATENT DOCUMENTS

| | | | |
|---|---|---|---|
| 4,559,827 | 12/1985 | Kupperman et al. | 73/644 |
| 4,571,693 | 2/1986 | Birchak et al. | 73/24.01 |
| 4,628,736 | 12/1986 | Kirby et al. | 73/590 |
| 4,679,160 | 7/1987 | Whitener | 73/632 |

OTHER PUBLICATIONS

"A Piezoelectric Ice Sensor for Aviation Applications", from May, 1990 issue of Sensors, pp. 13–33.

Primary Examiner—Hezron E. Williams
Assistant Examiner—Louis M. Arana
Attorney, Agent, or Firm—Griffin Branigan & Butler

[57] ABSTRACT

An apparatus and method for detection of icing onset and ice thickness upon an accretion surface utilizing ultrasonic echo ranging techniques, including propagation of ultrasonic waves through a buffer block. A portion of the wave energy is reflected by reference reflection means and another portion of the wave energy is propagated to the ice accretion surface and to a reflecting interface. The reflecting interface is represented either by the accretion surface in absence of icing, or by a thin ice layer at the icing onset, or by the ice/air interface of an ice layer accreted upon the accretion surface. Reflected waves are transduced to electrical signals. Relative signal amplitudes and time delays provide measures of particular icing conditions upon the accretion surface, and are appropriately resolved into calibrated signals indicating icing onset, ice thickness, and ice accretion rate.

30 Claims, 4 Drawing Sheets

APPARATUS AND METHOD FOR DETECTION OF ICING ONSET AND ICE THICKNESS This is a continuation of application Ser. No. 07/378,851, filed July 12, 1989, now abandoned.

BACKGROUND OF THE INVENTION

1. Field of the Invention

This invention relates to icing sensing systems for surfaces of vehicle structures, for instance aircraft structures and, more particularly, to an apparatus and a method for the detection of icing onset and ice thickness using ultrasonic echo ranging techniques.

2. Prior Art and Other Considerations

In general, icing upon surfaces of vehicles causes a variety of operational problems and may result in catastropic and life-threatening situations. In particular, for example, dangers of icing on aircraft surfaces are well known, and various measures are taken to reduce, avoid, and removing icing. In order to provide warning and quantitative indication of the degree and severity of ice accretion to facilitate initiation of such measures, whether under control of an operator or under automatic control, reliable and accurate detection of icing is an essential prerequisite.

Various ice detection devices are known in the art. For example, monitoring probes extending above the surfaces subject to icing provide some measure of icing, albeit in rather inaccurate and sometimes unreliable manners. Not only are protrusions above surfaces often undesirable and subject to damage, but such probes encounter icing conditions that are usually significantly different from the conditions prevailing upon actual vehicle surfaces. Another known is based upon measurement of surface capacitance changes that occur as a function of changes in the thickness of ice (the ice layer acting as a dielectric). However, the dielectric properties of ice are subject to significant variations depending on the type of ice, as for instance given by slush, glaze, rime etc., as well as by inclusions of dirt, dust, salts, and other materials. Consequently, capacitance measurement techniques have been relatively inaccurate. Optical methods have also been used, but are known to be hampered by optical-path obstructions due to substantially unavoidable dirt accretion.

A device for measurement of ice thickness employing ultrasonic, pulse-echo techniques is disclosed in U.S. Pat. No. 4,628,736 issued to Kirby et al. Kirby et al utilizes ultrasonic compression waves emitted into the ice by a transducer disposed at the accretion surface.. Reflections of the waves from the ice/air interface are received and detected by the transducer, and the time delay between emission and reception of the signals provides a measure related to the thickness of the ice.

It is well known in the art that compressional sound waves do not distinguish adequately between transmission into ice and water. Compression waves propagating into a water layer and reflecting off the water/air interface are practically indistinguishable from those propagating into an ice layer and reflecting from the ice/air interface. Thus, whereas the device taught by Kirby et al recognizes accretion on a surface layer, it is unable adequately to distinguish whether the layer is water or ice. Moreover, since the transducer device taught by Kirby et al is disposed at the accretion surface, thin accretion layers are not practically detectable because resulting reflected waves are received by the transducer while it is still saturated and ringing due to the initial transmission signal, whereby reliable detection of icing onset and of trace amounts of ice is precluded.

The apparatus and method of the present invention are objects to overcome the difficulties of the prior art and provide for the sensitive detection of the very onset of icing as well as the measurement of ice thickness and the distinction between water and ice.

SUMMARY

In accordance with principles of the present invention, an apparatus and a method for the detection of icing onset and ice thickness employ ultrasonic, echo-ranging techniques comprising at least one ultrasonic transducer and a buffer block in the wave propagation path between a transducer and an ice accretion surface. In this manner, the reception of echoes is delayed until after transducer saturation and termination of ringing due to the initial transmission signal. The buffer block includes a reference reflector for the generation of reference echo signals to eliminate varying effects in coupling between the transducer and the buffer block. At least one ultrasonic transducer for the generation and reception of sound waves is coupled to a first surface of the buffer block; and, a second surface of the buffer block is disposed at the ice accretion surface.

One ultrasonic transducer generates and transmits into the buffer block and receives therefrom ultrasonic shear waves. A further ultrasonic transducer is provided in an embodiment of the invention for the generation and transmission into the buffer block and reception therefrom of ultrasonic compression waves.

The shear wave transducer serves sensitively to detect the onset of icing without responding to a presence of water upon the accretion surface, and it provides accurate measures of ice-accretion thickness. The onset of icing is detected as an echo amplitude reduction and ice thickness is a function of the relative time delay of the echo signal reflected from the ice/air interface.

Another embodiment includes a compression wave transducer so that the measuring range is extended beyond a normal practical range limit for shear waves.

In use, an ultrasonic pulse emitted by a transducer propagates in the buffer block toward the ice accretion surface. A portion of the wave energy is reflected back to the transducer by a reference reflector disposed in the propagation path within the buffer block. This reflection is sensed by the transducer, and provides a reference signal. The wave also propagates to the accretion surface, is reflected therefrom, and is detected by the transducer to provide a corresponding signal. Shear waves propagating to and reflecting from the ice accretion surface facilitate detection of icing onset by sensitively detectable amplitude reduction of the reflected signal before accretion of an appreciable ice thickness. As ice accretes, its thickness provides a longer propagation path for the wave. The wave reflects from the ice/air interface; is detected by the transducer; and, provides a signal whose relative time delay (with respect to the reference signal) provides a measure of the ice-accretion thickness.

Signal amplitudes and relative time delays are resolved in appropriate resolver means to provide calibrated signals indicating icing onset, ice thickness, and accretion rate for operator attention and/or automatic initiation of deicing or other appropriate measures.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference numerals refer to like parts throughout different views. The drawings are schematic and not necessarily to scale, emphasis instead being placed upon illustrating principles of the invention.

DESCRIPTION OF THE PREFERRED EMBODIMENTS

Figure 1:
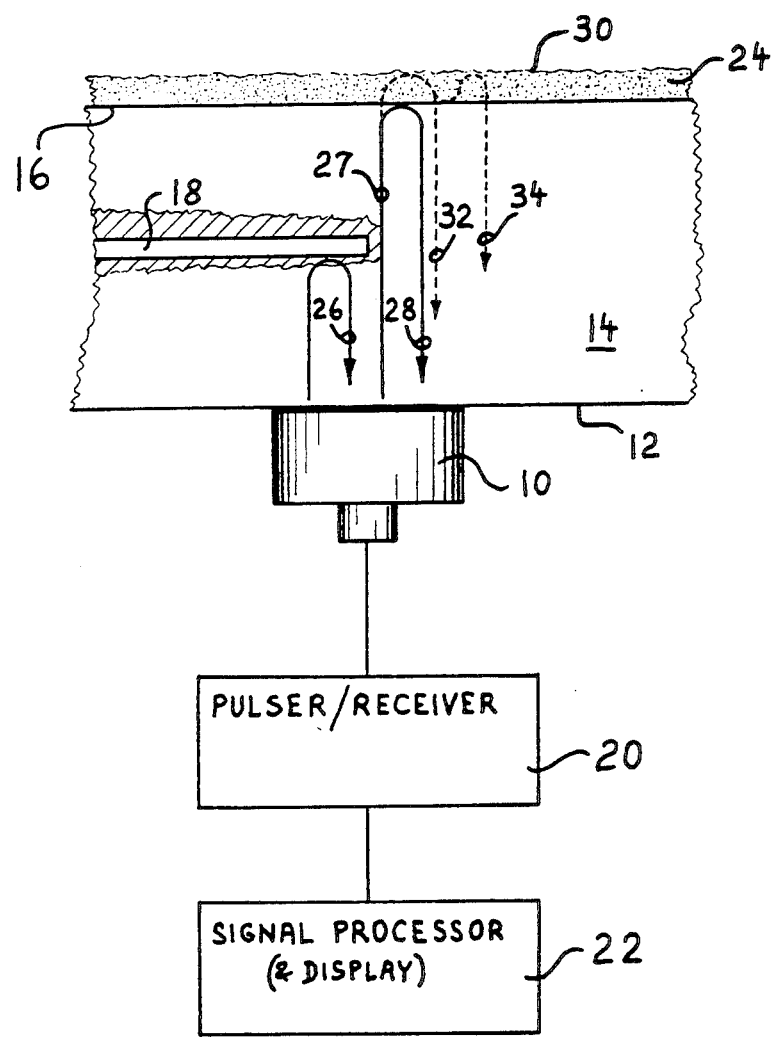
FIG. 1 is a schematic, partially-fragmented, sectional view and block schematic of apparatus according to the present invention.

Referring now to FIG. 1, a transducer 10 is disposed on a first surface 12 of a buffer block 14. Buffer block 14 further comprises a second surface 16 and reference reflector means 18—the latter being disposed in the region between first and second surfaces 12 and 16. Transducer 10 is electrically connected to a pulser/receiver 20, which in turn is connected to a signal processor 22 that can also include a signal display. An ice accretion 24 is indicated upon second surface 16.

Buffer block 14 is disposed with its second surface 16 in the plane of an ice accreting surface, for instance an aircraft wing surface or other vehicle surface upon which ice accretion is to be detected. In a preferred embodiment of the invention, the material of buffer block 14 is magnesium. However, various other solid materials can be used, provided that their ultrasonic impedances allow good matching to transducer 10 and to ice in an accretion upon second surface 16, while offering an adequate mismatch relative to air (in absence of an ice accretion) to cause distinct ultrasonic signal reflection back into buffer block 14 at the air interface of second surface 16.

Buffer block 14 provides an extended propagation path for ultrasonic signals transmitted thereinto by transducer 10 and for reflected signals propagating through buffer block 14 back to transducer 10. Consequently, a time delay is provided between the original transmission of an ultrasonic wave pulse from transducer 10 and the reception of echoes thereby. This time delay facilitates discrimination between these signals. Additionally, the provision of buffer block 14 allows disposition therein of reference reflector means 18.

Reference reflector means 18 comprises preferably a hollow hole, sawcut, or other cavity and serves to reflect a portion of the ultrasonic signal transmitted into buffer block 14 back to transducer 10. Preferably the cavity is filled with a gas (such as air, helium, or the like) and the cavity is sealed to avoid moisture condensation. The cavity may alternatively be filled with liquid or solid material of distinctly different ultrasonic impedance relative to the buffer block 14. The size, shape, and material of reference reflector means 18 are preferably chosen to provide approximately equal signal amplitudes of transducer-received echoes reflected from reference reflector means 18 and from second surface 16 (in absence of an accretion thereupon).

Transducer 10 can be a conventional piezoelectric, damped-wave ultrasonic transducer that serves to convert electrical signals into ultrasonic signals and vice-versa. Pulser/receiver 20 provides appropriate electrical signals to transducer 10 and receives echo signals transduced by transducer 10 for further processing. Signal processor 22 discriminates the various echo signals and resolves appropriate relationships therebetween, such as relative incidence times and relative amplitudes to provide indications of ice accretion conditions existing upon second surface 16. Such indications can be displayed and may be further used for initiation of deicing or other measures.

Transducer 10 is intimately coupled to buffer block 14, for instance by an ultrasonic couplant in form of an adhesive for a good match between the mating surfaces of buffer block 14 and transducer 10, as customarily used in similar situations. Additionally, transducer 10 is securely fastened to buffer block 14 by conventional mechanical means.

Pulser/receiver 20 generates electrical signals or pulses for transduction and transmission as ultrasonic signals by transducer 10. Signal processor 22 (partly cooperatively with pulser/receiver 20) provides timing for and between the transmitted ultrasonic wave pulses and performs other customary supervisory, control, and operator interfacing functions.

In response to appropriate electrical signals received from pulser/receiver 20, transducer 10 generates ultrasonic signals (pulses of waves) and transmits these signals into buffer block 14. A portion of the ultrasonic wave energy is reflected from reference reflector means 18 and is returned as a reference echo 26 to transducer 10 and is therein transduced to an electrical signal for further handling in pulser/receiver 20 and in signal processor 22. Another portion of the ultrasonic wave energy transmitted into buffer block 14, namely signal portion 27, propagates therethrough and is partially reflected by the second surface 16 (when ice accretion 24 is present) or is substantially totally reflected by second surface 16 (in absence of ice accretion 24). This reflected signal is returned as a detection echo 28 to transducer 10 and is therein transduced to an electrical signal for further handling in pulser/receiver 20 and in signal processor 22.

When ice accretion 24 is present on surface 16, as indicated in FIG. 1, a substantial portion of the ultrasonic wave energy, namely signal portion 27, transmitted into buffer block 14 past reference reflector means 18 propagates through second surface 16 and through ice accretion 24 and is reflected by ice/air interface 30. A portion of this reflection is returned to transducer 10 through buffer block 14 as an ice echo 32. It will be understood that multiple reflections of minor portions of the ultrasonic energy entering ice accretion 24 may be returned to transducer 10 in substantially attenuated and delayed manner. A first such multiple reflection is indicated in FIG. 1 as multiple echo 34.

Among the transducer-received echo signals, the present invention primarily utilizes reference echo 26, detection echo 28, and ice echo 32 to detect and measure ice accretion. As hereinbefore indicated, detection echo 28 originates from substantially total reflection of the portion of the ultrasonic energy reaching second surface 16 through buffer block 14 in absence of ice accretion 24. In presence of ice accretion 24, a substantial portion of the energy passes through surface 16, is reflected back from ice/air interface 30, and returns in somewhat attenuated form to transducer 10 as ice echo 32. The time delay between reception incidences of reference echo 26 and detection echo 28 is constant. The amplitude of detection echo 28 is reduced when ice accretion 24 is present. In presence of ice accretion, ice echo 32 is produced and provides a transducer signal whose time delay with respect to the reception incidence of reference echo 26 provides a measure of ice accretion thickness.

It will be appreciated that material properties of components of the apparatus, such as for instance given by ultrasonic impedances, and characteristics of the employed ultrasonic wave energy, etc. determine more specifically the propagation and reflection behaviour of the ultrasonic wave energy in the apparatus, as will be discussed in more detail hereinafter.

More particularly, the apparatus shown in FIG. 1, when employing ultrasonic compression waves, provides for the generation of a reference signal as a consequence of the reference echo 26 obtained from reference reflector means 18, as hereinabove described. Compression waves are reflected from an air interface, such as is given by second surface 16 in absence of an accretion thereupon or as given by ice/air interface 30 when an accretion is present. Buffer block 14 provides a sufficient propagation delay for the compression waves, so that reference echo 26 is received after subsidance of transducer saturation or ringing due to the initial transmitted wave pulse. Similarly, the delay in buffer block 14 provides for reception (by transducer 10) of echoes from second surface 16 (absence of accretion) or from ice/air interface 30 (presence of accretion) after adequate subsidance of transducer ringing due to reference echo 26.

The provision of buffer block 14 facilitates sensitive discrimination between transducer-transmitted signals and successively received echoes by avoidance of signal overlap. Moreover, buffer block 14, disposed in the ultrasonic signal propagation path, permits the provision of reference reflector means 18, whereby reference echo 26 is produced. Echo signals are referred to the amplitude and time incidence of reference echo 26 (as received by transducer 10), rather than to the originally transducer-transmitted signal, thusly immunizing the operation of the apparatus against changes in environmental parameters such as temperature and humidity which can cause variations in transducer-transmitted and received signals resulting in false accretion indications. Additionally, the character and amplitude of the signal generated by reference echo 26 provide indications of transducer malfunction and/or transducer separation from the buffer block 14.

Use of ultrasonic compressional waves in the apparatus of FIG. 1 is particularly advantageous for the measurement of relatively thick ice accretions because compressional waves propagate well into and in solids, such as ice, and are only moderately attenuated in ice. Moreover, as the propagation velocity of ultrasonic compression waves in ice is relatively high (3.8 mm per microsecond), the separation of ultrasonic signals (including echoes) needed for accurate and sensitive ice accretion thickness measurement favors measurement of thicker ice accretions. Discrimination between echoes and, therefore, accurate thickness measurement becomes increasingly difficult for thinner accretions and tends to be impractical, if not infeasible, for ice accretion thicknesses representing icing onset conditions and up to about one to several millimeters of ice thickness.

Reliable early detection of icing onset, however, is of great importance, particularly upon aircraft surfaces. Additionally, it is also important to distinguish between actual ice accretions and water. A difficulty associated with the use of ultrasonic compression waves, in this respect, is in that such waves propagate into water relatively easily and, therefore, are practically incapable of distinguishing between ice and water layers upon a surface. Echoes of compression waves transmitted into a water layer (and reflected off the water/air interface) are indistinguishable from echoes obtained from reflection off an ice/air interface through an ice layer.

According to principles of the present invention, in order to reliably and sensitively detect and measure not only onset of icing and relatively thin ice accretions, but also to accurately distinguish between the presence of water and ice accretion, an embodiment of the present invention employs ultrasonic shear waves in the apparatus of FIG. 1.

Use of ultrasonic shear waves is particularly advantageous for the measurement of relatively thin ice accretions because such waves propagate in ice at a relatively low velocity of about 1.8 mm per microsecond. Consequently, the thereby increased separation of ultrasonic signals including echoes (in time) facilitates more accurate and sensitive ice accretion thickness measurement—particularly for measurement of thinner accretions. Moreover, as ultrasonic shear waves do not substantially propagate into water, their employment permits practical and reliable distintion between ice and water accretions. Ultrasonic shear waves experience relatively high attenuation (particularly in ice), which effect is utilized according to principles of the invention sensitively to detect icing onset upon an ice accretion surface. For the purpose of this discussion, icing onset should be understood as an accretion of ice deposits having thicknesses in a range that preclude practical detection and measurement by techniques of measuring ultrasonic signal propagation time through such ice deposits.

According to principles of the invention, detection of icing onset is performed by employing ultrasonic shear waves transmitted into buffer block 14 (as hereinbefore described in conjunction with FIG. 1) by transducer 10, receiving reference echo 26 and detection echo 28 (and/or ice echo 32), and resolving the time delay and the relative amplitude (or amplitude ratio) therebetween. The operation of the apparatus is originally set and calibrated to provide, in absence of an accretion (on second surface 16), a known fixed amplitude ratio between reference echo 26 and detection echo 28. This ratio is preferably one to one, but it can be established at any fixed value providing distinctly resolvable signal amplitudes for individual echoes. Additionally, the operation of the apparatus is calibrated to set its output signals to indicate zero ice accretion thickness corresponding to the time delay obtained between reference echo 26 and detection echo 28 in absence of any ice accretion.

In use of the apparatus, when icing onset occurs, signal portion 27 of the transmitted ultrasonic shear wave penetrates into the thin ice deposits (of an icing onset) and is reflected by the ice/air interface back to transducer 10 via buffer block 14 as detection echo 28 (and/or ice echo 32). In view of the significant attenuation of shear wave energy in ice layers (even in very thin deposits representing icing onset), particularly also as a consequence of multiple reflections between interfaces, detection echo 28 (and/or ice echo 32) arrives at transducer 10 with a distinctly decreased amplitude in comparison with the amplitude of detection echo 28 obtained in the absence of icing. Consequently, discrimination of relative amplitudes or of the change in amplitude ratio of reference echo 26 and detection echo 28 (and/or ice echo 32) detects icing onset before increases of the time delay between these echoes become practically discernible.

As ice accretion increases, such time delays become discernible and resolvable and provide a measure of ice accretion thickness. For instance, it has been found that the onset of icing corresponding to an ice deposit of a thickness of less than about 0.05 mm is practically, clearly, and distinctly detectable by an apparatus employing shear waves according to the present invention. In this situation, the amplitude of detection echo 28 (and/or ice echo 32) has been reduced to approximately one half of the (calibrated) echo amplitude obtained in absence of any icing. As icing thickness was increased to approximately 0.4 mm of glaze ice, a clearly resolvable time delay between detection echo 28 and ice echo 32 was obtained already well below this thickness.

In respect to the aforesaid reduction of the amplitude of detection echo 28 due to icing onset and an accretion of ice, the following considerations apply in regard to choices of material and therewith ultrasonic impedance for buffer block 14. For ease of detection of icing onset, a large amplitude reduction is desired upon occurrence of icing onset, but at the same time a still substantial transmission of ultrasound energy into the accreting ice layer should be facilitated to serve ice thickness detection by measurement of the propagation delay through the ice layer. The reduction in amplitude of the ultrasonic signal across the interface between the buffer block 14 and the ice layer depends on the relative impedances of the buffer block material and the ice. Specifically, the involved amplitude ratio is approximately proportional to the ratio between the difference and the sum of the ultrasonic impedances of the two materials. This ratio should be chosen to be significantly less than unity, and a preferred ratio for the apparatus of the invention employing shear waves is about 0.5, as the impedance of the magnesium material preferably chosen for the buffer block is approximately 3 to 3.2 times the impedance of ice.

Apparatus according to the invention employing ultrasonic shear waves is particularly useful for detection of icing onset and ice thickness in a thickness range up to more than one quarter of an inch, and it is operated at an ultrasonic center frequency of about 5 MHz or somewhat higher, employing a highly-damped piezoelectric shear wave transducer. The ability to measure ice thickness improves with increasing frequency and with increased damping properties of the employed transducer. However, practical and economic trade-off considerations provide the aforesaid preferred choice of about 5 MHz for the ultrasonic frequency at this time.

Apparatus according to the invention employing ultrasonic compression waves is particularly useful for detection of larger ice thicknesses from about one eighth of an inch upward, when operated at an ultrasonic center frequency of about 5 MHz or somewhat lower, employing a highly-damped piezoelectric compression wave transducer.

Figure 1A:
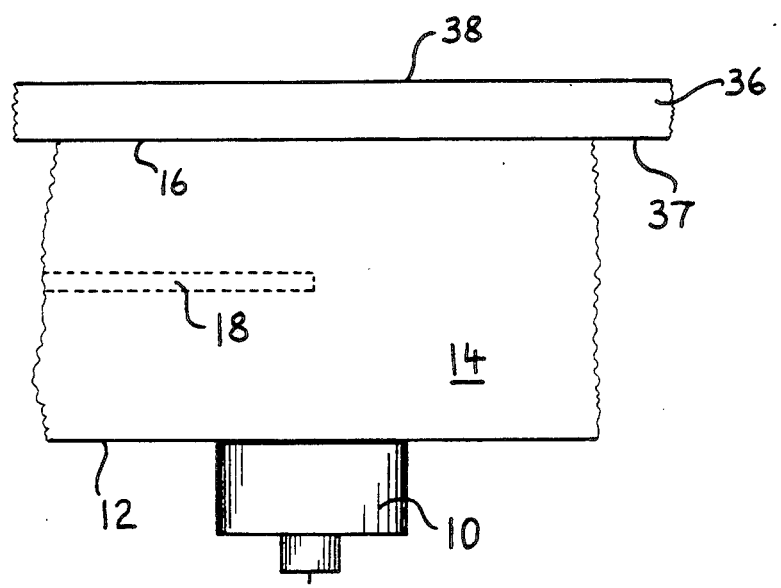
FIG. 1A is a schematic fragmented view of a portion of FIG. 1 including a surface member.

The apparatus of FIG. 1A includes a surface member 36 having an inner face 37 in intimate contact with the second surface 16 of buffer block 14. In this embodiment, the second surface 16 does not serve as the ice accretion surface, but an accretion face 38 upon surface member 36 serves this purpose. Buffer block 14 is here disposed below surface member 36 which can be, for instance, an aircraft wing covering or other vehicle facing upon which ice accretion is to be detected. One reason for such an arrangement is, for example, that cut-outs or openings in aircraft surfaces to accomodate a buffer block directly (as indicated by FIG. 1) may be undesirable in many cases for reasons of stress, corrosion, etc. If an acoustic mismatch arises or undesirable multiple echoes occur, however, either the FIG. 1 structure should be used or other steps should be taken to correct the mismatch. It will also be appreciated that satisfactory coupling between the second surface 16 of buffer block 14 and inner face 37 of surface member 36 (and to accretion face 38) must be provided to ensure that ultrasonic wave energy propagates therethrough without undue attenuation and excessive reflections. For this reason also ultrasonic impedances of surface member 36 and buffer block 14 are appropriately matched and a couplant can be used, for instance in form of a conventional adhesive, for a good intimate contact and a match between the mating surfaces. Additionally, buffer block 14 is securely fastened to surface member 36 by conventional mechanical fastening means.

Figure 2:
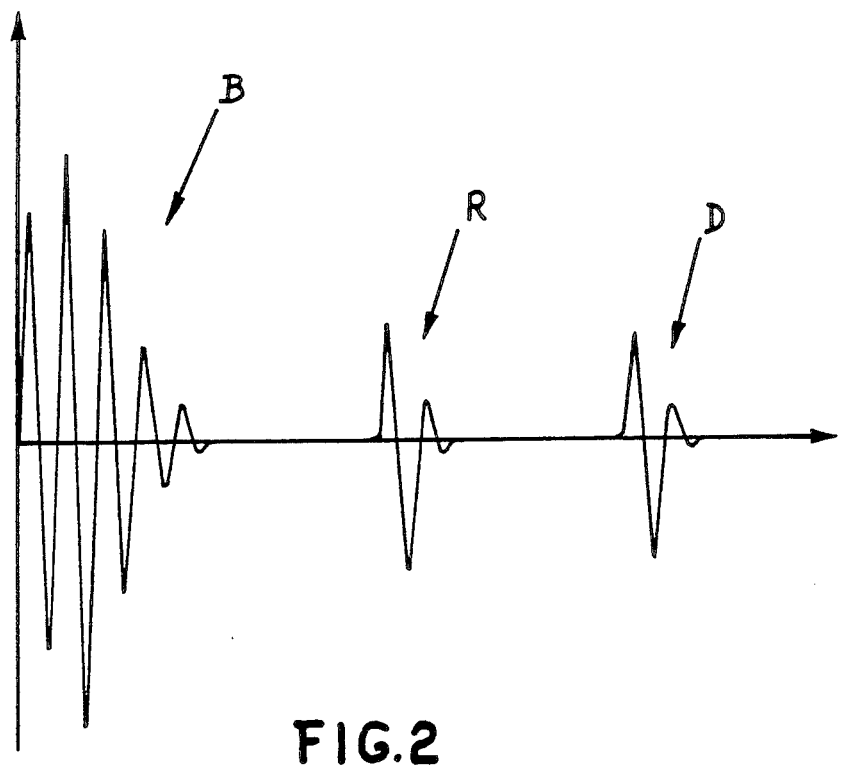
FIGS. 2 and 3 are schematic diagrams indicating transducer-received echo signals obtained in an apparatus as shown in FIG. 1 and 1A.
Figure 3:
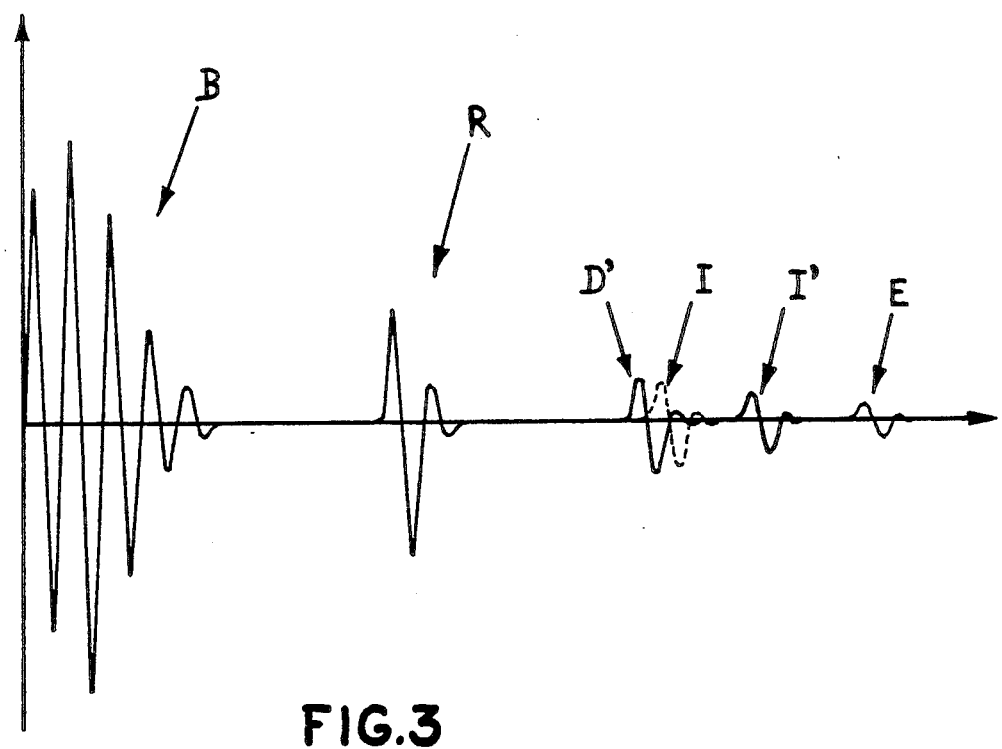

Referring now to the diagrams in FIGS. 2 and 3, the therein schematically depicted transducer signals are plotted in dependence of time—the ordinate indicating amplitude and the abscissa indicating time. A transmission signal B represents the response of transducer 10 (shown in FIG. 1) to a short-duration electrical signal sent thereto by pulser/receiver 20, including ringing of the transducer. In a preferred embodiment, this electrical signal had a center frequency of about 5 MHz. It is pulsed at regular, comparatively-long intervals which at least exceed the time for return of utilized echoes. A reference signal R represents the response of transducer 10 to reference echo 26.

In FIG. 2, a detection signal D represents the response of transducer 10 to detection echo 28. In absence of an ice accretion upon the second surface 16 of buffer block 14, detection signal D is delayed in relation to reference signal R by a constant time to which the apparatus is precalibrated. An accretion of ice increases this time delay which is accordingly resolved in signal processor 22 to provide a measure of ice accretion thickness. The diagram in FIG. 2 schematically represents transducer signals in an apparatus employing ultrasonic compression or shear waves, and more particularly also schematically represents transducer signals in an apparatus employing ultrasonic shear waves in absence of icing onset and without any ice accretion.

The diagram in FIG. 3 represents transducer signals in an apparatus employing shear waves during icing onset and/or in presence of an ice accretion. Upon onset of icing, the amplitude of signal D (indicated in FIG. 2) is attenuated, as hereinbefore described, and icing onset signal D' (shown in FIG. 3) results. Icing onset signal D' is resolved with respect to the precalibrated amplitude of reference signal R (and detection signal D) by signal processor 22 and thusly provides sensitive detection and a measure of icing-onset conditions.

As ice accretion increases (past icing onset), an ice signal I separates in time from signal D' and becomes more and more discernible. Ice signal I is generated in response to ice echo 32, indicated in FIG. 1. The time delay of ice signal I relative to reference signal R (and detection signal D or signal D') is then resolved by signal processor 22 and thereby provides a measure of the thickness of ice accretion. Ice signal I is further indicated in FIG. 3 as ice signal I', representing conditions of accretion of a substantial ice thickness.

FIG. 3 also shows an echo signal E that corresponds to a first of multiple echoes 34 (indicated in FIG. 1). Signal E is generally of a significantly reduced amplitude in comparison with other signals and does not play a role in the detection of ice accretion according to the present invention.

Figure 4:
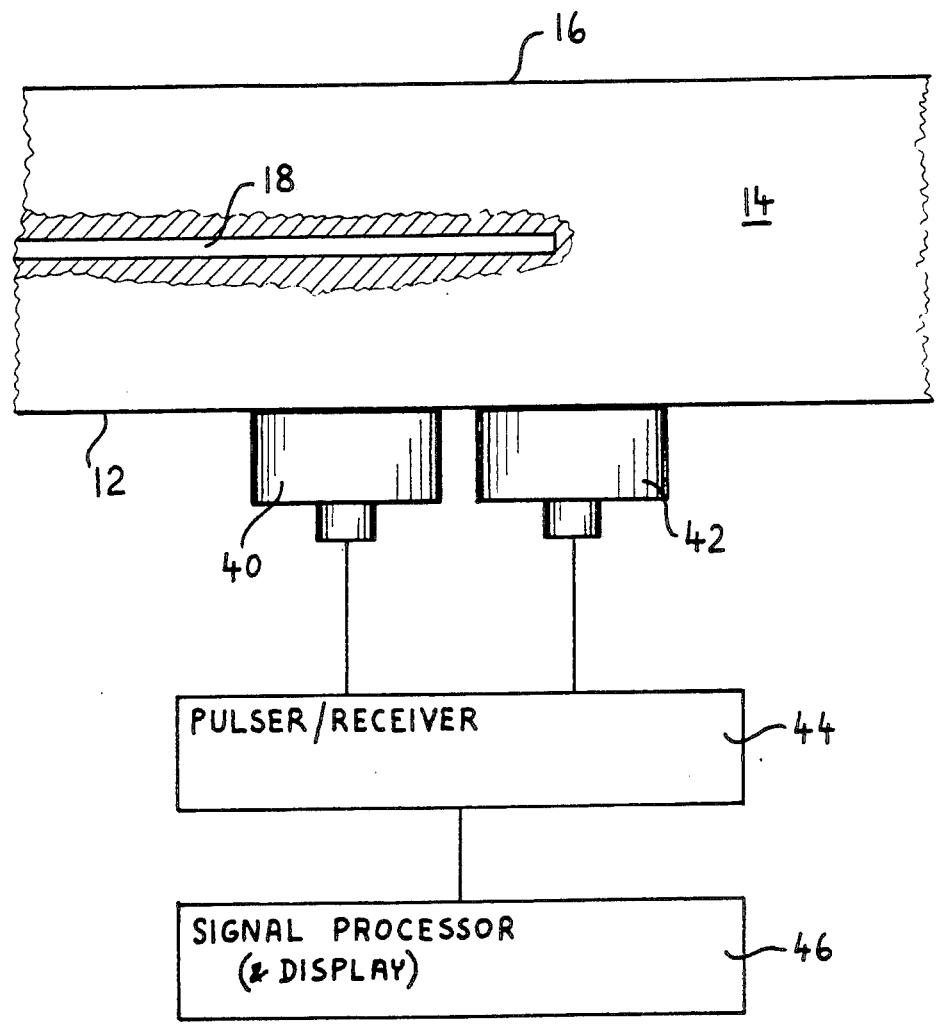
FIG. 4 is a schematic, partially -fragmented, sectional view and block schematic of another embodiment of the invention.

Referring now to FIG. 4, an embodiment of the present invention is schematically depicted that is particularly advantageous for detection of ice accretions over extended thicknesses and that, at the same time, is capable of sensitively and accurately detecting icing onset and very thin ice accretions, while being able to clearly distinguish between ice and water deposits. Similarly to the depiction in FIG. 1 (and in FIG. 1A), a buffer block 14 is provided, having a first surface 12 and a second surface 16 and comprising reference reflector means 18. A shear wave transducer 40 and a compression wave transducer 42 are disposed in intimate contact with first surface 12. Transducers 40 and 42 are electrically connected to a pulser/receiver 44, which in turn is connected to a signal processor 46.

The arrangement shown here is substantially the same as the arrangement of FIGS I and IA, except that buffer block 14 serves here simultaneously for propagation of both shear and compression waves. Also two respective transducers are mounted on buffer block 14 and are provided with electrical circuitry in pulser/receiver 44 and signal processor 46 to serve both transducers and to resolve shear and compression wave signals. Similarly, fundamental operation is substantially the same as hereinbefore described for an apparatus according to the present invention employing compression waves and for an apparatus according to the invention employing shear waves, although both devices are here combined into one arrangement.

A main reason for this combination is the provision of a single apparatus to detect and measure ice accretion sensitively and accurately over extended thickness ranges, between onset of icing and to thicknesses substantially in excess of one quarter of an inch. As hereinbefore described, employment of shear waves in an apparatus according to principles of the invention provides such detection up to approximately one quarter of an inch or so of ice accretion thickness, and is therefore particularly suited to operate in this range. For situations requiring detection of ice accretions in excess of this range, supplementary employment of compression waves which are particularly suited for detecting such thicker accretions is adopted here.

It will be appreciated that a combination apparatus, as depicted in FIG. 4, employs preferably overlapping thickness-detection ranges between the shear and compression wave portions of the apparatus, and that signal processor 22 includes therefor appropriate discrimination circuitry.

In any of the hereinabove described embodiments of the invention, output signals (and displays thereof) are provided by respective signal processors (22 and 46) in a form most appropriate to the particular use. These output signals and displays include indication of icing onset, ice accretion thickness, and in some cases ice accretion rate. The latter is obtained in the signal processor in customary manner by processing ice accretion thickness changes in relation to time.

With regard to transducer sizes employed in any of the hereinabove described embodiments of the invention, transducers in a size range between 0.25 and 1.5 inches in diameter have been found particularly suitable preferred diameters are in the range of about 0.25 to 0.5 inches. However, no fundamental reasons exist that might preclude employment of other sizes.

While the invention has been particularly shown and described with reference to preferred embodiments thereof, it will be understood by those skilled in the art that various changes and modifications in form and details may be made therein without departing from the spirit and scope of the invention.

The embodiments of the invention in which an exclusive property or privilege is claimed are defined as follows:

1. Apparatus for detection of icing onset and ice accretion employing ultrasonic pulse-echo techniques, said apparatus including an ice-accreting surface and comprising:

means for transducing electrical signals to and from ultrasonic signals, said means for transducing including means for transmitting and receiving ultrasonic shear waves;

buffer means including first and second surfaces and reference reflector means, said second surface being coupled to said ice-accreting surface, said first surface being coupled to said means for transducing for receiving ultrasonic signals therefrom and for transmitting ultrasonic echo signals thereto, said reference reflector means being operative partially to reflect ultrasonic signals that are transmitted thereto through said first surface from said means for transducing back through said first surface to said means for transducing in the form of reference-echo signals;

said buffer means being operative in providing a propagation time delay for ultrasonic signals propagating therethrough so that ultrasonic signals emitted from said means for transducing have substantially subsided therein prior to arrival thereat of ultrasonic echo signals, including reference echo signals, that have had their origin in the emitted ultrasonic signals;

pulser/receiver means electrically coupled to said means for transducing for providing electrical signals thereto to effect transmission of corresponding ultrasonic signals therefrom and for receiving electrical echo signals corresponding to ultrasonic echo signals received by said means for transducing; and, means for resolving electrical echo signals received from said pulser/receiver means in relation to reference echo signals received from said pulser/receiver means to obtain electrical detection signals corresponding to icing onset and ice accretion conditions upon said ice-accreting surface;

wherein said ice-accreting surface substantially reflects ultrasonic shear waves even if water is present thereupon, wherein ultrasonic signals propagate into an ice accretion in presence thereof upon said ice-accreting surface and reflect from an ice- /air interface of the ice accretion in a discriminatably delayed manner in relation to reference echo signals reflected from said reference reflector means, and wherein ultrasonic shear waves are reflected substantially at said ice-accreting surface during icing onset thereupon in a discriminatably attenuated form in relation to reference echo signals reflected from said reference reflector means.

2. Apparatus according to claim 1, wherein said means for transducing further includes means for transmitting and receiving ultrasonic compression waves.

3. Apparatus according to claim 1, wherein said means for resolving includes signal processor means electrically coupled to said pulser/receiver means, said signal processor means being operative in handling electrical echo signals and in supervising and controlling the operation of said pulser/receiver means, said signal processor means comprising means for operator interfacing therewith.

4. Apparatus of claim 1, wherein a surface member is interposed between said second surface and said ice-accreting surface, said second surface being coupled to said ice-accreting surface through said surface member.

5. Apparatus according to claim 1, wherein said second surface comprises said ice-accreting surface.

6. Apparatus according to claim 3, wherein said signal processor means include means for display of electrical detection signals corresponding to icing onset and ice accretion conditions upon said ice-accreting surface.

7. Apparatus according to claim 1, wherein said reference reflector means comprises a cavity.

8. Apparatus of claim 7, wherein said cavity defines a hole in said buffer means.

9. Apparatus of claim 7, wherein said cavity is sealed with respect to ambient.

10. Apparatus of claim 7, wherein said cavity is filled with a liquid having an impedance substantially different from the impedance of said buffer means.

11. Apparatus of claim 7, wherein said cavity is filled with a solid having an impedance substantially different from the impedance of said buffer means.

12. Apparatus of claim 7 wherein said cavity is sealed and filled with a gas.

13. Apparatus of claim 12 wherein said gas is air.

14. Apparatus according to claim 1, wherein a ratio of the difference divided by the sum of the impedances of said buffer means and ice is substantially less than unity.

15. Apparatus of claim 14, wherein said ratio is about 0.5.

16. Apparatus according to claim 1, wherein the material of said buffer means is essentially magnesium.

17. Apparatus in accordance with claim 1, said buffer means having an impedance that is about 3 times the impedance of ice.

18. Apparatus in accordance with claim 1, wherein said means for transducing comprises at least one highly damped transducer.

19. Apparatus of claim 18, wherein said at least one highly damped transducer comprises a piezoelectric element.

20. Apparatus of claim 19, wherein said piezoelectric element has a diameter in an approximate range of 0.25 to 1.5 inches.

21. Apparatus of claim 19, wherein said piezoelectric element has a diameter in a preferred range of about 0.25 to 0.5 inches.

22. Apparatus of claim 18, wherein said means for transducing has a center frequency of about 5 MHz.

23. Apparatus of claim 18, wherein said means for transducing has a center frequency in excess of 5 MHz.

24. Apparatus of claim 18, wherein said means for transducing has a center frequency below 5 MHz.

25. Apparatus in accordance with claim 1, wherein said means for transducing comprise at least one shear wave transducer and at least one compression wave transducer.

26. A method for detecting ice upon an ice-accreting surface, including detecting of icing onset, employing ultrasonic pulse-echo techniques including use of ultrasonic shear waves, the method being effected by an apparatus that includes transducer means coupled via buffer means to said ice-accreting surface, said buffer means including a reference reflector therein, the method comprising the steps of:

(a) transmitting initial ultrasonic signals by said transducer means into said buffer mean toward said ice-accreting surface;

(b) receiving ultrasonic echo signals of said initial ultrasonic signals by said transducer means from said buffer means, said ultrasonic echo signals including reference-echo signals, icing-presence detection signals, and icing-onset detection signals, said icing-onset detection signals using shear waves;

(c) partially reflecting said initial ultrasonic signals from said reference reflector to provide said ultrasonic reference-echo signals;

(d) reflecting portions of said initial ultrasonic signals from an ice/air interface of an ice accretion in the presence thereof upon said ice-accreting surface to provide said ultrasonic icing-presence detection signals, said ultrasonic icing-presence detection signals being discriminatably delayed in relation to said ultrasonic reference-echo signals in correspondence with the thickness of said ice accretion;

(e) reflecting portions of said initial ultrasonic signals that use shear waves substantially at said ice-accreting surface during icing onset thereat to provide said ultrasonic icing-onset detection signals, said ultrasonic icing-onset detection signals being discriminatably attenuated in relation to said ultrasonic reference-echo signals as a consequence of said icing onset;

(f) transducing said ultrasonic echo signals received by said transducer means to corresponding electrical echo signals and resolving the electrical signals corresponding to said icing-presence detection signals and to said icing-onset detection signals in relation to the electrical signals corresponding to said reference-echo signals to obtain electrical detection signals corresponding to ice-accretion and icing-onset conditions at said ice-accreting surface;

said buffer means providing an ultrasonic propagation time delay for said initial ultrasonic signals and for said ultrasonic echo signals so that said ultrasonic echo signals arrive after subsidence of transmitted initial ultrasonic signals in said transducer means.

27. The method according to claim 26, further including using ultrasonic compression waves in steps (a) through (d) and (f).

28. The method according to claim 26, including the step of processing said electrical detection signals to provide indication of ice-accretion rate.

29. The method according to claim 26, including the step of displaying a representation corresponding to said ice-accretion and icing-onset conditions.

30. The method according to claim 26, wherein said step (f) includes the steps of:
  discriminating the time delay between receipt of said reference-echo signals and said icing-presence detection signals; and,
  discriminating the relative amplitudes between said reference-echo signals and said icing-onset detection signals received by said transducer means.

* * * * *